United States Patent
Alessi

(10) Patent No.: US 9,906,845 B2
(45) Date of Patent: Feb. 27, 2018

(54) SENSING DEVICE AND CORRESPONDING APPARATUS AND METHOD

(71) Applicant: STMicroelectronics S.r.l, Agrate Brianza (IT)

(72) Inventor: EnricoRosario Alessi, Catania (IT)

(73) Assignee: STMicroelectronics S.r.l., Agrate Brianza (MB) (IT)

( * ) Notice: Subject to any disclaimer, the term of this patent is extended or adjusted under 35 U.S.C. 154(b) by 0 days.

(21) Appl. No.: 15/251,248

(22) Filed: Aug. 30, 2016

(65) Prior Publication Data

US 2017/0289649 A1 Oct. 5, 2017

(30) Foreign Application Priority Data

Mar. 31, 2016 (IT) .................. 102016000033040

(51) Int. Cl.
| | | |
|---|---|---|
| *G01C 5/06* | (2006.01) | |
| *G08B 21/18* | (2006.01) | |
| *H04Q 9/00* | (2006.01) | |
| *G08B 5/22* | (2006.01) | |

(52) U.S. Cl.
CPC .............. *H04Q 9/00* (2013.01); *G01C 5/06* (2013.01); *G08B 5/222* (2013.01); *H04M 2250/12* (2013.01); *H04Q 2209/43* (2013.01); *H04Q 2209/823* (2013.01)

(58) Field of Classification Search
CPC ......... G01C 5/06; G01S 5/0263; G08B 5/222; H04W 4/025; H04W 4/028; H04Q 9/00
USPC .............. 340/539.11, 539.13, 601; 342/462; 701/118, 119
See application file for complete search history.

(56) References Cited

U.S. PATENT DOCUMENTS

| | | |
|---|---|---|
| 7,162,368 B2 | 1/2007 | Levi et al. |
| 8,180,591 B2 * | 5/2012 | Yuen ............... A61B 5/0002 |
| | | 702/160 |
| 8,676,480 B2 * | 3/2014 | Lynch ............... G01C 21/3694 |
| | | 340/995.13 |
| 2006/0100782 A1 | 5/2006 | Levi et al. |
| 2011/0106449 A1 | 5/2011 | Chowdhary et al. |

(Continued)

FOREIGN PATENT DOCUMENTS

WO 2015105678 A2 7/2015

OTHER PUBLICATIONS

Carrasco. R.C. et al.: "Probabilistic Finite-State Machines—Part I," IEEE Transactions on Pattern Analysis and Machine Intelligence, IEEE Computer Society, Jul. 1, 2005, pp. 1013-1025, vol. 27, No. 7.

(Continued)

*Primary Examiner* — Hung T Nguyen
(74) *Attorney, Agent, or Firm* — Slater Matsil, LLP

(57) ABSTRACT

A sensing device includes a barometric sensor, e.g., MEMS-based, and a processing unit coupled to the barometric sensor to receive therefrom a barometric signal. The processing unit is configured as a state machine having a plurality of states including an initial state and a final state with a set of transitions from the initial state to the final state. The transitions are triggered by the barometric signal reaching one or more triggering thresholds. The processing unit may include an expert system sensitive to state data and altitude data from the state machine for recognizing the final state being reached.

23 Claims, 6 Drawing Sheets

(56) References Cited

U.S. PATENT DOCUMENTS

2014/0171068 A1* 6/2014 Marti .................. G01S 1/047
 455/427
2015/0198443 A1 7/2015 Yi et al.
2015/0247917 A1 9/2015 Gum et al.
2016/0062364 A1* 3/2016 Foinet .................. A63H 27/14
 701/2

OTHER PUBLICATIONS

Komeda, K. et al., "User Activity Recognition Method Based on Atmospheric Pressure Sensing," UBICOMP 14 Adjunct, Sep. 13-17, 2014, 10 pages.

Sankaran, K. et al., "Using Mobile Phone Barometer for Low-Power Transportation Context Detection," 12th ACM Conference on Embedded Networked Sensor Systems (SenSys 2014), Nov. 3-6, 2014, 15 pages.

Vanini, S. et al., "Adaptive Context-Agnostic Floor Transition Detection on Smart Mobile Devices," 2013 IEEE International Conference on Pervasive Computing and Communications Workshops, Mar. 18-22, 2013, 6 pages.

* cited by examiner

SENSING DEVICE AND CORRESPONDING APPARATUS AND METHOD

CROSS-REFERENCE TO RELATED APPLICATIONS

This application claims priority to Italian Patent Application No. 102016000033040, filed on Mar. 31, 2016, which application is hereby incorporated herein by reference.

TECHNICAL FIELD

The disclosure relates to sensor devices. One or more embodiments may relate to altitude sensors for apparatus such as, e.g., wearable and smart phone apparatus.

BACKGROUND

Sensing and communication modules for, e.g., mobile phones and other mobile devices may provide location and context-aware information and services.

Low-power absorption, low latency and high accuracy may represent desirable features for a such modules.

Also, an ever increasing number of applications provide location and context features. For instance, the ability to discriminate user activity and user location may rely on the processing of "primitive" information provided by sensors "on-board" of an application device (e.g., a smart phone or a smart watch).

Processing may provide information on certain user activities such as travel mode (e.g., with the capability of sub-typing a pedestrian behavior as stationary, walking, fast walking, running, climbing or descending staircases, riding a bicycle, being conveyed on a vehicle, shopping, watching TV, sleeping, waking-up). Based on such information an application apparatus may propose tasks and/or provide various functions such as monitoring, alert or control functions.

An effective floor/altitude change detection scheme may provide environment information based on primitive data from a pressure/barometric sensor thus making it possible, e.g., to determine the location of a user and/or facilitate discriminating activity detection, possibly in combination with information derived from other sensors.

Additional activity information such as climbing or descending staircases, possibly in combination with calculated speed based on pressure/barometric data may be useful in alerting a user by possibly providing safety messages. Also, detection of floor/altitude changes, optionally in combination with staircase slope information and/or step counting may be used, e.g., in computing burned calories.

Despite the intensive innovation activity in that area, the need is still felt for improved solutions, especially as regards making a sensing device less sensitive to noise, including "environmental" noise: a mobile phone or a smart watch being affected by movements of the hands and the gait of the user may be exemplary of such sources of noise.

SUMMARY

One or more embodiments provide a sensing device that is less sensitive to noise, including "environmental" noise, such as, a mobile phone or a smart watch being affected by movements of the hands and the gait of the user may be exemplary of such sources of noise.

One or more embodiments may also relate to corresponding apparatus, a corresponding method as well as a computer program product loadable in the memory of at least one processing device (e.g., a DSP) and including software code portions for executing the steps of the method when the product is run on at least one computer.

As used herein, reference to such a computer program product is understood as being equivalent to reference to a computer-readable medium containing instructions for controlling the processing system in order to co-ordinate implementation of the method according to one or more embodiments.

The claims are an integral part of the disclosure of one or more exemplary embodiments as provided herein.

One or more embodiments may provide a sensing device for altitude (e.g., level/floor) change detection including a barometric pressure sensor and logic circuitry, possibly in combination with a supervisor module acting as a decisional system.

One or more embodiments may include a logic supervisor module adapted to be trained on-the-field, e.g., for reconstructing context parameters such, e.g., a building structure and/or a floor height.

One or more embodiments may provide a sensing device with the ability of detecting the manner in which level or floor is changed, e.g., by using a staircase or a lift (elevator).

One or more embodiments may include a low-power pressure/barometer sensor based, e.g., on MEMS (Micro Electro-Mechanical Systems).

One or more embodiments may include a real time clock (RTC) for a time-based feature extraction.

One or more embodiments may include interface and control units for smart GPS applications, including, e.g., wearable devices and/or indoor navigation systems.

One or more embodiments may be configured for exploiting input from other sensors.

One or more embodiments may provide a robust decision on level changes possibly involving information from other sensors such as an accelerometer or a pedometer, thus reducing the risk of mis-classification.

One or more embodiments may be applied to smart phones and other wearable functions for human safety, possibly based on information derived from altitude change information, possibly supplemented with information from other sensors.

One or more embodiments may be applied to smart phones and wearable functions for fitness, adapted to rely on information derived from a sensor device possibly in combination with additional sensors.

One or more embodiments may be applied in indoor navigation systems exploiting floor change detection for improved understanding of user scenario and position.

BRIEF DESCRIPTION OF THE DRAWINGS

One or more embodiments will now be described, by way of example only, by referring to the annexed figures, wherein.

DETAILED DESCRIPTION OF ILLUSTRATIVE EMBODIMENTS

Figure 1:
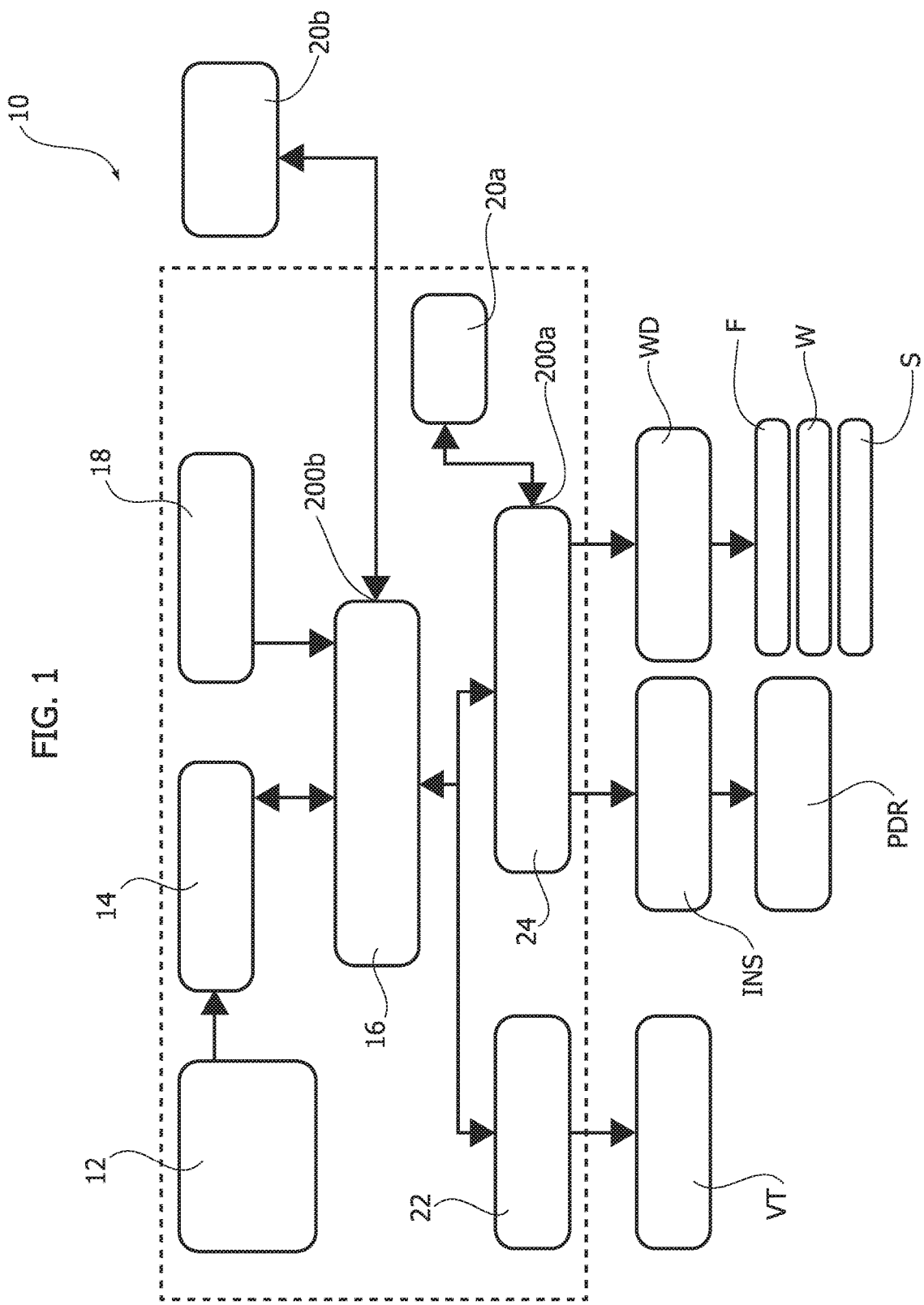
FIG. 1 is a general block diagram of a sensor architecture including one or more embodiments.

In the ensuing description, one or more specific details are illustrated, aimed at providing an in-depth understanding of examples of embodiments of the present disclosure. The embodiments may be obtained without one or more of the specific details, or with other methods, components, materials, and so on. In other cases, known structures, materials or operations are not illustrated or described in detail so that certain aspects of embodiments will not be obscured. Reference to "an embodiment" or "one embodiment" in the framework of the present description is intended to indicate that the particular configuration, structure, or characteristic described in relation to the embodiment is comprised in at least one embodiment. Hence, phrases such as "in an embodiment" or "in one embodiment" that may be present in one or more points of the present description do not necessary refer to one and the same embodiment. Moreover, particular conformations, structures, or characteristics may be combined in any adequate way in one or more embodiments.

The reference used herein are provided merely for convenience and hence do not define the extent of protection or the scope of the embodiments.

Effective floor/altitude detection and additional extracted features related to activity of a user may provide useful environment information for a variety of mobile applications, thus facilitating improving performance of mobile devices such as mobile phones and other wearable devices.

In-door navigation systems and/or position location systems (e.g., so-called Personal Dead Reckoning—PDR position location systems) provide examples of applications that may take advantage of the availability of such a sensing device.

Background information concerning altitude change detection may be derived from documents such as:

K. Komeda et al.: "User Activity Recognition Method based on Atmospheric Pressure sensing"—UBICOMP '14 ADJUNCT, Sep. 13-17, 2014, SEATTLE, Wash., USA;

S. Vanini et al.: "Adaptive context-agnostic floor transition detection on smart mobile devices", 10$^{th}$ IEEE Workshop on Context Modeling and Reasoning 2013, San Diego (18 Mar. 2013), pp. 2-7;

K. Sankaran et al.: "Using Mobile Phone Barometer for Low-Power Transportation Context Detection", SenSys '14, Nov. 3-6, 2014, Memphis, Tenn., USA;

WO 2015/105678 A2; and

US 2006/0100782 A1 (to which U.S. Pat. No. 7,162,368 B2 corresponds).

The last cited document indicates that, in some implementations, obtaining relative and/or absolute elevation information within a building by using a navigation device may be helpful. For instance, a fireman entering a burning building may be facilitated in understanding what floor he/she is on while being unable to use a conventional navigation device to determine such a current floor.

Solutions for sensing, e.g., a floor change may be based on the following principle:

when a person is in a building and moves from one floor to another, the barometric pressure at his or her current position changes, when the pressure difference (gap) between a current pressure value and a pressure value detected, e.g., at a source floor reaches a certain threshold, a climbing/descending activity may be detected, when the pressure level becomes stationary again at a "destination floor", a floor change may be detected.

An underlying problem of such an approach is that pressure data may be affected by a level of noise, including sources of noise deriving from environmental conditions. In the case of a mobile device such as a mobile phone or a smart watch, additional sources of noise may be related to movements of the hands of the user and/or the gait of the user. These sources of noise may render altitude sensing intrinsically "weak", that is prone to error.

One or more embodiments may provide an altitude sensor device 10 including a barometric sensor 12.

As used herein "altitude", is intended to be comprehensive of other designations such as "floor" or "level." Consistently, designations such as "altitude sensing" or "altitude sensor" will be generally applicable to designate sensing devices and procedures adapted for detecting floor and/or level information. Similarly, the designation "barometric sensor" will be generally comprehensive of any type of device configured or adapted to detect pressure.

The (MEMS-based) pressure sensors available with the Applicant company under the designations STUVIS25 or LPS22HB may be exemplary of such a sensor 12.

Exemplary features of a LPS 22 HB pressure sensor include the following:

260 to 1260 hPa absolute pressure range,
a current consumption down to 4 μA,
high overpressure capability: 20× full-scale,
embedded temperature compensation,
24-bit pressure data output,
16 bit temperature data output,
output data rate up to 75 Hz,
SPI and I$^2$C interfaces,
embedded FIFO and filtering,
interrupt functions: Data Ready, FIFO flags, pressure thresholds,
supply voltage: 1.7 to 3.6 V, and
high shock survivability: 22,000 g.

Figure 2:
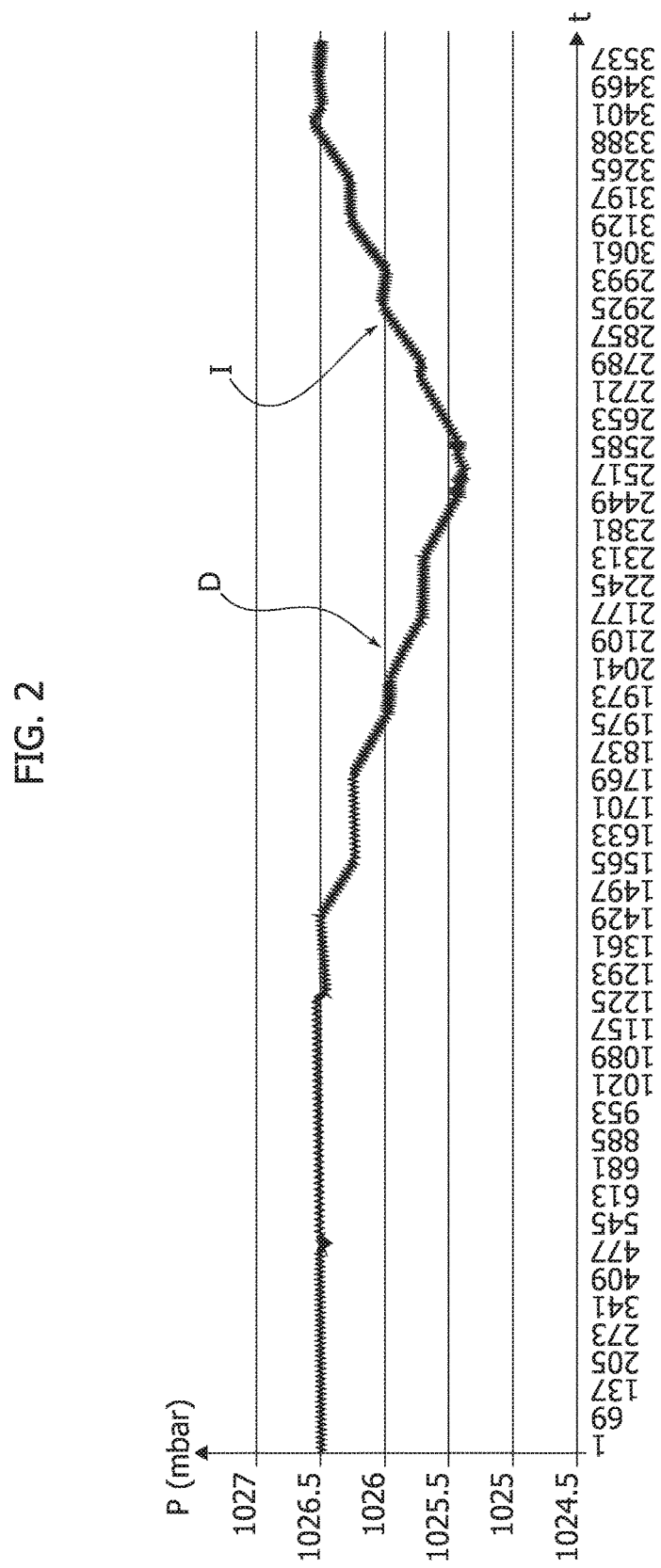
FIG. 2 is a diagram exemplary of an output signal from a barometric pressure sensor.

The diagram of FIG. 2 is exemplary of a pressure signal P (plotted in a mbar scale) as provided by such a sensor a set of subsequent samples over a time scale t (abscissa).

A pressure drop D as exemplified in FIG. 2 may thus be exemplary of an increase in altitude (e.g., moving up in a building) while a pressure increase I as similarly portrayed in FIG. 2 may be exemplary of moving down in a building.

One or more embodiments may be based on the concept of integrating a barometric sensor 12, e.g., of the type exemplified in the foregoing, with a set of sub-units for interfacing, e.g., an indoor navigation system, a smart Global Positioning System—GPS, wearable devices of various kinds with the ability of detecting altitude (e.g., floor or level changes).

In one or more embodiments the integrated sensing device 10 may be able to support other user activities and context layout feature extraction. In one or more embodiments, this may involve the use of various other external sensors such as, e.g., motion sensors of various kinds, gas sensors, compass sensors.

In one or more embodiments, these sensors may be used for enabling the integrated sensing device 10. For instance, an indoor-outdoor detection sensor may be used for activating an altitude change (e.g., floor change) detection function in the main logic of the sensing device 10.

In one or more embodiments, other sensors may be used for improving (e.g., making more robust) a decision about an altitude change such as a floor or level change and/or possible feature extraction processes.

For instance, in one or more embodiments, an accelerometer and/or a pedometer may be used for confirming that a pressure change may be reliably related to, e.g., movement from one floor to another in a building.

The probability of false detections induced by external (noise) sources, possibly including noises which result in rapid change in air pressure may thus be reduced, optionally by making it possible to discriminate between different ways of movements, e.g., by climbing/descending a staircase or by using a lift (elevator). Also, this may involve the capability of providing context-based addressing of demands for features such as low power absorption, low latency and high accuracy, thus making the device 10 suitable for applications, e.g., in the field of wearable devices and environmental sensors.

In one or more embodiments, as exemplified in the block diagram of FIG. 1, a (high accuracy) barometric sensor 12 as discussed in the foregoing may be coupled to an analog front end (AFE) 14 adapted to process in a manner known per se (e.g., by A/D conversion, level translation, and so on) in order to feed a barometric signal (see, e.g., signal P in FIG. 2) to a logic unit 16 (e.g., a DSP), whose operation may be timed by a real time clock (RTC) 18.

In one or more embodiments, the logic unit 16 may be configured to get the raw data coming from the sensor 12, convert them to digital (if not already done in the front end 14) and process them in order to control other sub-units.

In one or more embodiments, the logic unit 16 may co-operate with various sensors 20a, 20b in order to exploit information provided by these sensors for enabling an altitude (e.g., floor or level) change feature.

An accelerometer and/or a pedometer may be exemplary of such sensors.

These sensors may include "internal" sensors incorporated in the sensing device 10 (e.g., 20a), sensors "external" to the sensing device 10 (e.g., 20b), or both internal sensors 20a and external sensors 20b.

Co-operation of the logic unit 16 with those sensors may be either direct (as exemplified in FIG. 1 for sensor(s) 20b) or through other blocks such as the enabler module 24 to be discussed later (as exemplified in FIG. 1 for sensors 20a).

It will be otherwise appreciated that the representation of FIG. 1 is merely exemplary, in that, in one or more embodiments, the logic unit 16 may co-operate directly with "internal" sensors 20a while co-operating with "external" sensors 20b via other blocks.

In one or more embodiments, the logic unit 16 may be configured for implementing, e.g., an expert system for pattern recognition adapted to exploit barometric information from the sensor 12 (e.g., via the front end 14) possibly in conjunction with information from other sensors 20a, 20b.

In one or more embodiments, the logic unit 16 may be configured to provide a feature extraction module able to extract features for dedicated sub-units again based on the barometric signal from the sensor 12 (e.g., via the front end 14), possibly in conjunction with information provided by other sensors 20a, 20b.

In the block diagram of FIG. 1, the enabler modules 22 and 24 are representative of an altitude change detection condition 22 and a floor change detection condition 24, respectively.

As indicated at the outset of this description, the term "altitude" detection is herein intended to be comprehensive of more specialized functions such as floor or level change detection.

In one or more embodiments, general information concerning altitude changes, as provided by the enabler module 22 may be exploited for functions such as vehicle tracking VT. In one or more embodiments, such tracking function may be based on the exploitation of information as provided by the barometric sensor 12 in combination with information provided by other sensors such as an accelerometer, a magnetometer and/or a gyroscope.

A more specialized altitude change information as represented by a floor or level change detection condition as provided by the enabler module 24 may be exploited, e.g., by an indoor navigation system INS possibly associated with a pedestrian dead reckoning system PDR and/or one or more wearable devices WD for, e.g., health, fitness, wellness or sport applications generally denoted F, W and S.

In one or more embodiments, the real time clock 18 may provide information about timing for, e.g., for computing feature extraction parameters possibly based on timing.

In one or more embodiments, the logic unit 16 may include, in a manner known per se, features for controlling sub-units expected to interface external processing units, such as external micro-processors for dedicated functions such as a smart GPS, indoor navigation and wearable devices.

Figure 3:
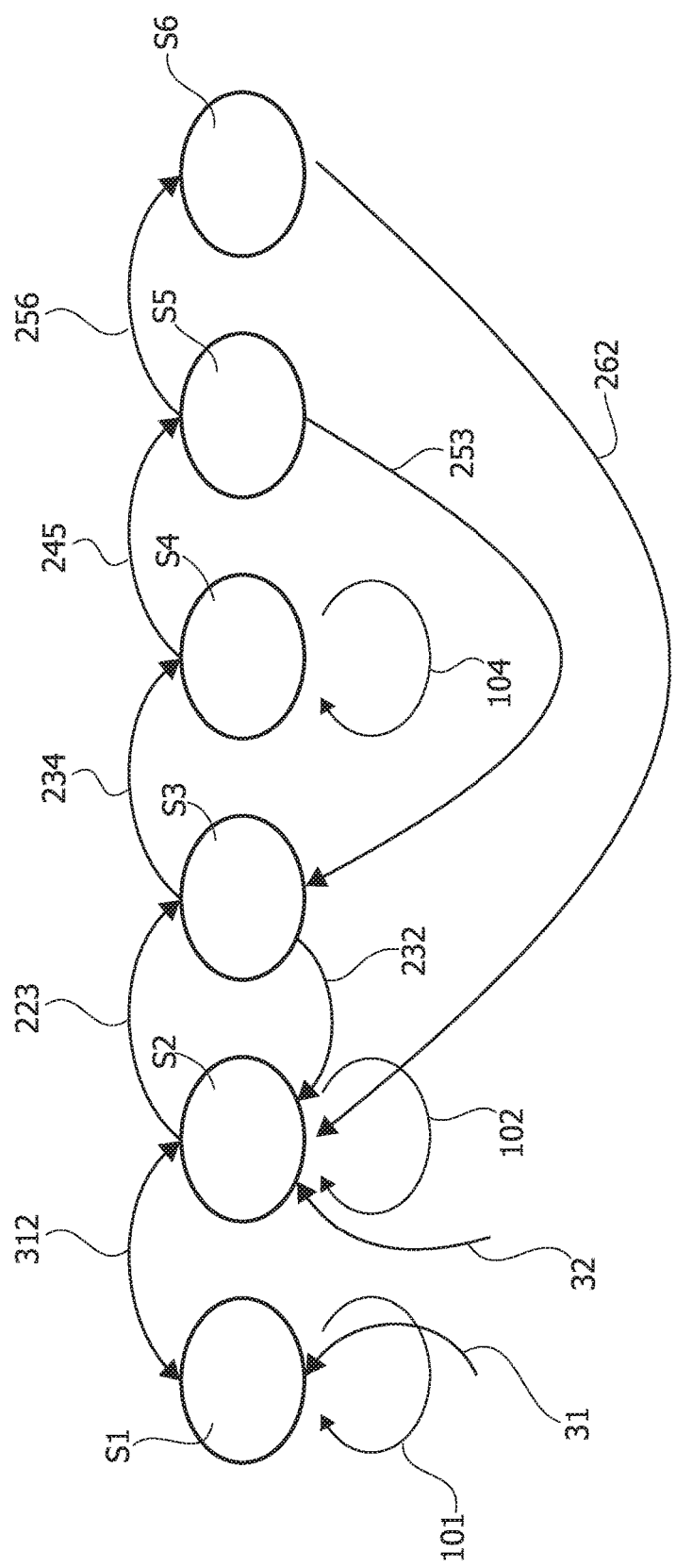
FIG. 3 is exemplary of state machine according to one or more embodiments.
Figure 4:
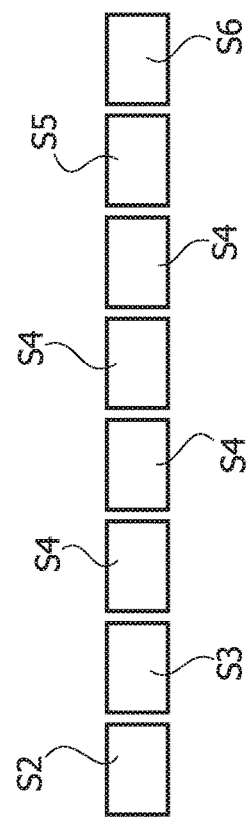
FIG. 4 is exemplary of possible operation of a machine according to FIG. 3, FIGS. 5 and 6 are flow-charts exemplary of possible signal processing in one or more embodiments.

FIG. 3 is a graph exemplary of possible operation of the logic unit 16 which may facilitate reducing sensitivity of the sensing device 10 to various sources of noise (disturbance). FIG. 4 is an example of sequence of states adapted to be generated by such a method.

Operation as exemplified in FIG. 3 may be regarded as exemplary of event-driven operation of a (finite) state machine—FSM whose state may change as a function of external events.

As used herein, the designation state machine is applied to a machine which can be in one of a number of states, the machine being in one state at a time with the ability to change from one state to another (that is undergo a transition) upon to a triggering event of condition. Such a state machine may thus be defined by its states and the triggering conditions for the transitions therebetween.

In one or more embodiments, event-driven operation may involve state changes (transitions) according to a graph as exemplified in FIG. 3, with a sequence of states suitable to be used by a supervisor module, e.g., for pattern recognition as exemplified in FIG. 4.

In one or more embodiments as exemplified in FIG. 3 altitude (e.g., level) changes may be detected in response to user activity, e.g., staircase climbing being detected. In one or more embodiments, the same underlying principle may be extended to detecting other ways of a changing altitude, e.g., by using a lift. In one or more embodiments, how (namely the way or manner) altitude is changed, e.g., by climbing or descending a staircase or, alternatively, by using a lift may be detected.

For instance, states S1 to S6 exemplified in FIG. 3 may be exemplary of the following conditions of a wearer of a sensing device 10 (or apparatus including such a sensing device 10):

S1: wearer sitting;
S2: wearer walking;
S3: wearer starting climbing a staircase;
S4: climbing a staircase in process;
S5: climbing a staircase ended;
S6: altitude (level or floor) changed.

According to current graph formalism, an event failing to lead to a transition may be represented by a line "looping" over an "old" state as exemplified, e.g., at 101, 102 and 104 (for states S1, S2 and S4, respectively).

Events leading to a change/transition from one state to another are indicated by arrows pointing to the "new" state starting from the "old" state as exemplified at 223 (from state S2 to state S3), 234 (from state S3 to state S4), 245 (from state S4 to state S5), 256 (from state S5 to state S6), 232 (from state S3 back to state S2), 253 (from state S5 to state S3), and 262 (from state S6 to state S2).

Finally, arrows pointing to a state, e.g., 312 (pointing to states S1 and S2) or 31 (pointing to state S1) or 32 (pointing to state S2) are representative of such a state being triggered by a certain event.

For instance (this presentation is merely for exemplary purposes) states S1, S2 may be representative of the wearer (of the sensing device 10 (or apparatus including such a sensing device 10) being either sitting or walking. Either state may be triggered, e.g., by a sensor (e.g., 20a or 20b) such as, e.g., a pedometer (double arrow labeled 312) or by an indoor/outdoor detection sensor, included, e.g., among sensors 20b of FIG. 1.

In one or more embodiments, operation of the state machine of FIG. 3 may be as a function of a signal, designated Gradient, representative of the variation of the barometric signal P from the sensor 12 (that is of the altitude or height) between a previous position and a current position (e.g., separated by a certain number of samples in FIG. 2), e.g., $$\text{Gradient} = P(\text{CurrentHeight}) - P(\text{PreviousHeight})$$

Looping over state S1 (sitting—see 101) may thus be indicative of the wearer having maintained a sitting position, while looping over the state S2 (walking—see 102) may be due to any variations, e.g., in the barometric signal P being (e.g., in modulus) less than a certain threshold TH_START, that is:

$$|\text{Gradient}| < TH\_START.$$

This may be indicative either of the wearer being seated or of the wearer walking by essentially moving in a horizontal plane, without experiencing any appreciable changes in altitude.

Conversely, transition (e.g., at 223) from state S2 (walking) to state S3 (start climbing) may be dictated by the barometric signal P experiencing a variation reaching the threshold, e.g., $$|\text{Gradient}| \geq TH\_START.$$

The variation in the barometric signal P returning after a time interval (as dictated, e.g., by the clock 18) under the threshold, e.g., $$|\text{Gradient}| < TH\_START$$

may cause the system to return to state S2. This may be indicative of a temporary transition due "noise" as possibly represented by a small jump in the wearer's gait.

If, conversely, the amplitude of the variation gradient remains above the threshold for a longer time, that is $$|\text{Gradient}| \geq TH\_START,$$

may cause the system to transition (e.g., at 234) to state S4.

This may be indicative of the wearer being climbing or descending (depending on the sign of the variation, e.g., Gradient) a staircase, with the system looping over state S4 (see 104) as long as such a condition ($|\text{Gradient}| \geq TH\_START$) is maintained.

A drop in the altitude variation modulus, namely $$|\text{Gradient}| < TH\_START$$

may be indicative of climbing/descending being ended, which may lead the system to transition (e.g., at 245) to state S5.

In state S5 a comparison may be made of the cumulated difference in altitude (e.g., Delta H) in the climbing/descending process as represented by states S3, S4, S5.

The cumulated altitude variation Delta H may be compared (e.g., in modulus) against a respective threshold TH_DELTA. This may be representative of a certain level change corresponding, e.g., of an altitude variation which may be held to be representative of change between two floors in a building.

In one or more embodiments, if |Delta H|<TH_DELTA, the system may evolve back to state S3, which may be indicative of the climbing/descending activity being held unable to represent, e.g., a level change likely to correspond to change of floor (up or down) in a building.

This may be representative, e.g., of a situation where the wearer of a sensing device 10 (or apparatus including the sensing device 10) decides to move down after a few steps of the stairs.

Additionally, sources of noise may generate P (altitude) values and thus gradients that make it possible to cross the whole state chain until state S5.

The condition |Delta H|<TH_DELTA may thus permit to go back to state S3 if the condition on Delta H is not verified, by protecting operation from false detections of level changes due to noise. This (first) level of protection may be supplemented by a second level of protection as represented by a supervisor module as discussed in the following.

If, conversely, |Delta H|>TH_DELTA, then the system may evolve (see 256) to state S6, indicative of, e.g., a change in a altitude (level) expectedly representative of a change of floor (up or down) in a building.

At this point, the system may evolve from state S6 back to state S2 (or state S1) so that the process described in the foregoing may take place again in order to detect a possible (further) altitude variation representative of, e.g., climbing or descending towards another floor in the building.

While exemplified as prompted in connection with climbing or descending a staircase (e.g., as a function of a pedometer signal), processing as exemplified in FIG. 3 may be prompted as a function of another signal, e.g., an accelerometer signal adapted to detect a vertical displacement resulting from the wearer of a sensing device 10 (or apparatus including the sensing device 10) having moved up or down a building by means of a lift.

In one or more embodiments, a level change by lift may be detected with the same procedure discussed in the foregoing. In that case the value for Gradient may be higher due to the wearer using a lift instead of a staircase.

In one or more embodiments, the way of changing level (staircase/lift) may be identified by introducing a respective threshold TH_START_LIFT and condition in the S3 state, with looping line 104 operating as discussed above. A condition |Delta H|>TH_START_LIFT or TH_START may thus permit to discriminate respectively the way of changing level by lift of by climbing/descending a staircase, overall operation being otherwise as discussed previously in connection with FIG. 3.

In either case, a sequence of states as exemplified in FIG. 4 may be exemplary of such an altitude variation being detected.

Figure 5:
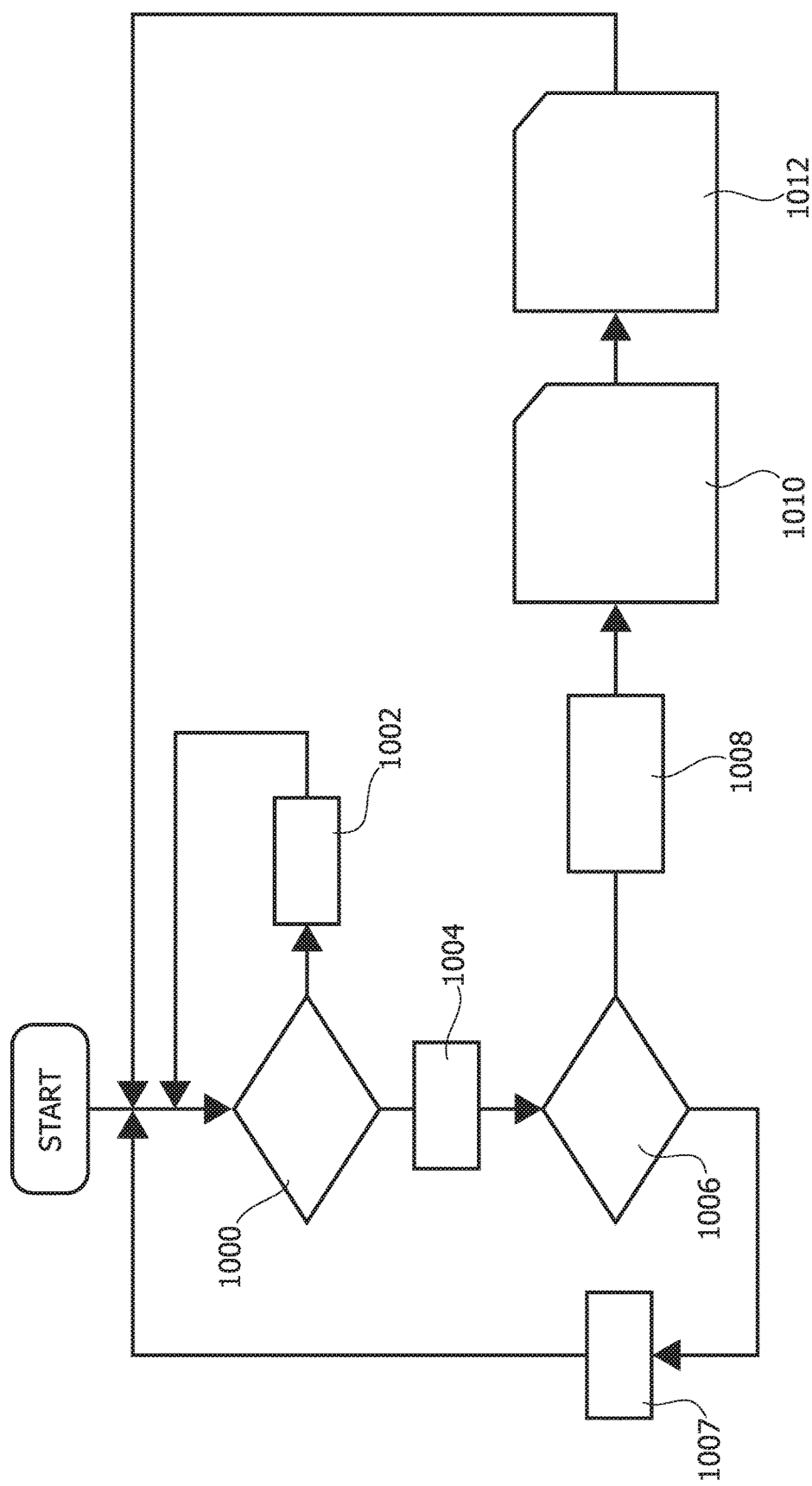

The flow chart of FIG. 5 is exemplary of possible processing according to the pattern outlined in FIG. 3.

After a START phase, in a step 1000 a check may be effected (based on a signal provided by, e.g., an indoor/outdoor sensor—20b, or possibly 20a) as to whether the wearer is located indoor (that is in a building) or outdoor.

In one or more embodiments, if an outdoor location is detected (which may be held unlikely to be associated to moving up or down in a building) the system merely loops (e.g., through wait step 1002) upstream of step moo.

If conversely, an "indoor" state is detected (step 1004) processing may be started along the lines of FIG. 3 as a function, e.g., of a signal provided by a pedometer (able to detect walking and climbing/descending a staircase—steps S2 to S5) as represented by the decision step 1006 in the flow chart of FIG. 5.

In the same flow chart, block 1008 is representative of possible "looping" over the state S1 (sitting) or S2 (walking in a horizontal plane) see 101 or 102 in FIG. 3.

Alternatively, if in a step 1006 walking/running (indoor in the example considered) is detected, in a step 1008 current altitude (height) can be detected (starting, e.g., from an initial status of walking and/or by using a reference starting value) so that climbing/descending (that is level or floor variation) may be detected in a step 1010 (see state S6 in FIG. 3) as discussed in the foregoing.

At that point, a pattern recognition and/or feature extraction activity may be performed in a step 1012 as exemplified better in the flow chart of FIG. 7 (which will be discussed in the following).

Figure 6:
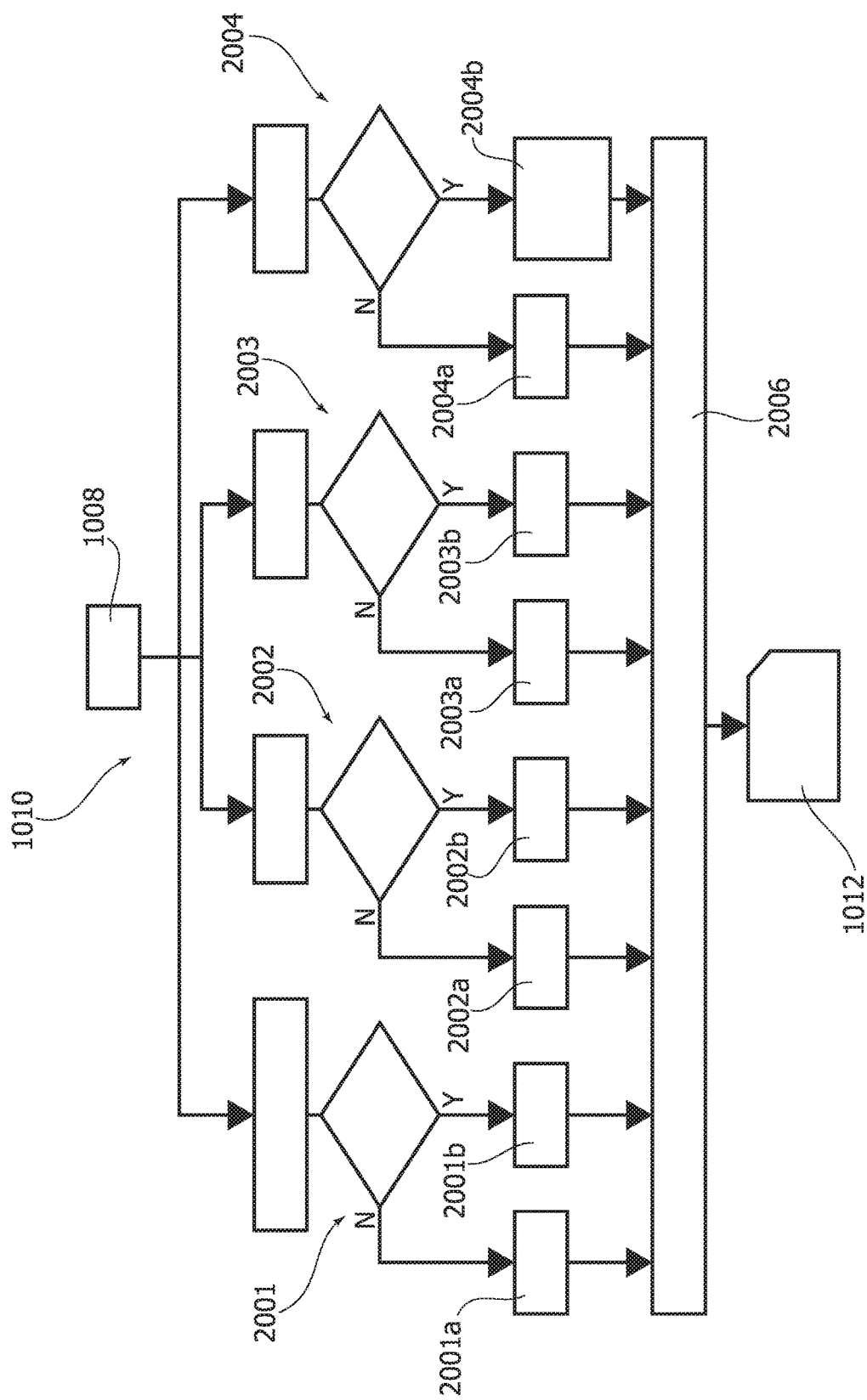

The flow chart of FIG. 6 is an exemplary representation of climbing status detection (block 1010 in FIG. 5).

A starting point in the flow chart of FIG. 6 may be represented by the block 1008 (previous status/current height) in the flow chart of FIG. 5.

From there, the system may evolve to various comparison steps with thresholds TH_START and TH_DELTA adapted to detect any of the following:
previous state is walking or running (step 2001),
previous step is climbing start (step 2002),
previous state is climbing in process (step 2003),
previous state is climbing/descending ended (step 2004).

The various blocks 2001a to 2004b are exemplary of possible outcomes of the steps 2001 to 2004, such as e.g.:
2001a: walking or running state is maintained (see, e.g., 102 in FIG. 3);
2001b: state is changed to climbing/descending start (see, e.g., 223 in FIG. 3);
2002a: state is returned to walking or running (see, e.g., 232 in FIG. 3);
2002b: state evolves to climbing/descending in process (see, e.g., 234 in FIG. 3);
2003a: climbing/descending in process confirmed (see, e.g., 104 in FIG. 3);
2003b: state is changed to climbing/descending ended (see, e.g., 245 in FIG. 3);
2004a: climbing/descending is (re)started (see, e.g., 253 in FIG. 3);
2004b: state evolves to S6 (see, e.g., 256 in FIG. 3).

Block 2006 in FIG. 6 is exemplary of state values being loaded to a state buffer (included or coupled to the logic unit 16) while altitude values (that is values for the pressure signal P) may be loaded to a data buffer (similarly included or coupled to the logic unit 16).

In one or more embodiments such buffers may include circular buffers with, e.g., 100 state values.

Figure 7:
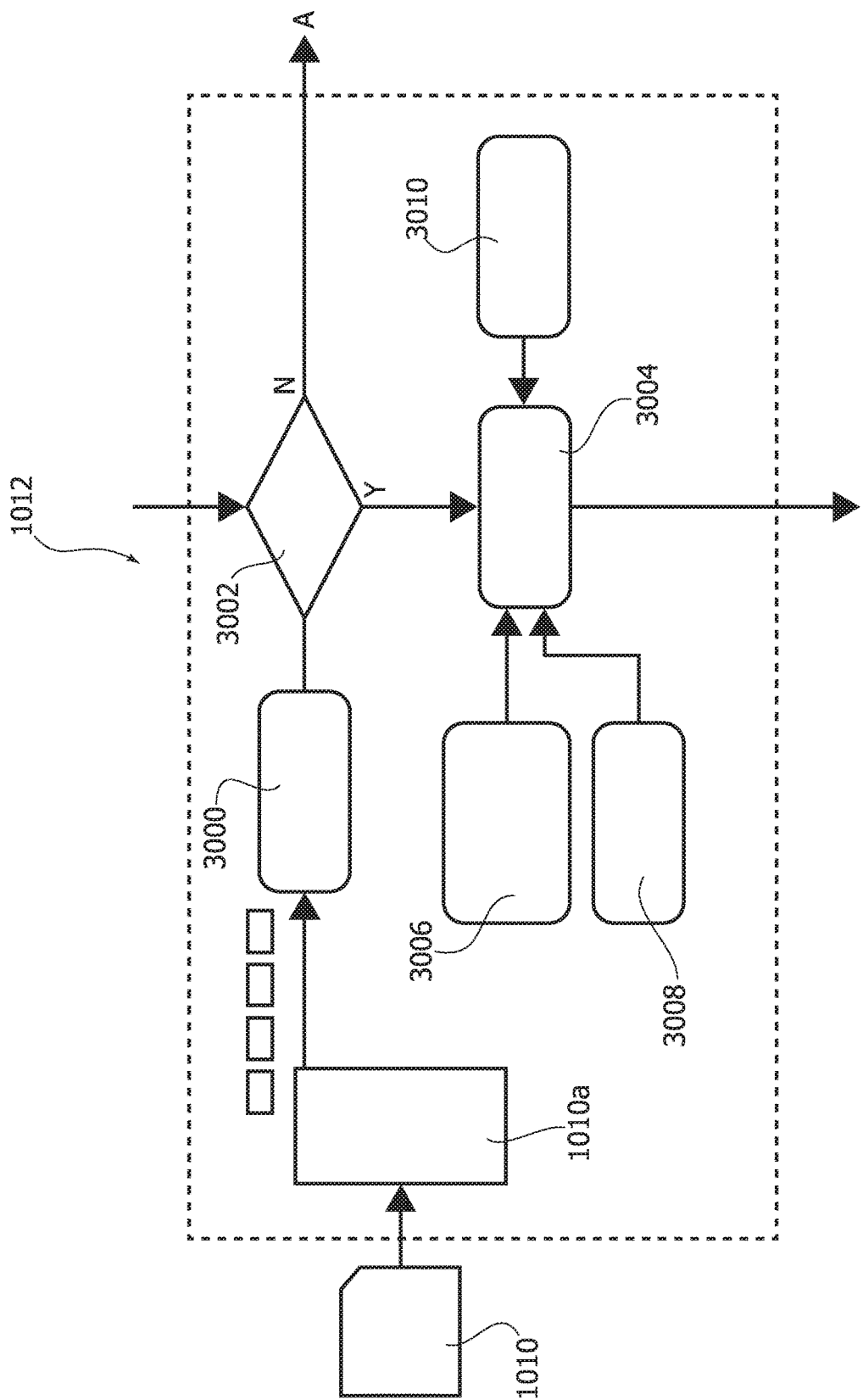
FIG. 7 is a functional block diagram exemplary of a possible system layout including one or more embodiments.

In one or more embodiments certain parameters may be extracted, e.g., to be loaded to a parameter buffer (again included or coupled with the logic unit 16) for possible use in pattern recognition by an expert system adapted to be implemented, e.g., in the logic unit 16, e.g., along the lines of the functional diagram of FIG. 7.

In the block diagram of FIG. 7, 1010 denotes climbing status detection as discussed in the foregoing with respective data 1010a (e.g., as read from a state buffer and/or a data buffer for altitude data 1010) fed to an expert system 3000 to perform pattern recognition tasks.

Such an expert system (adapted to be configured according to known principles) may include a supervisor to provide decisions about, e.g., floor or level change detection (see state S6 in FIG. 3).

If no such change is determined (e.g., negative outcome N of step 3002 in FIG. 7), operation may return to point A upstream of block 1000 in FIG. 5.

If, conversely an altitude (e.g., floor or level) change is detected (e.g., positive outcome Y of step 3002 in FIG. 7), the system may evolve to a feature extraction step 3004 aiming at, e.g., determining a certain set of features which may be used in an altitude-dependent context.

The related processing may involve e.g.:
collecting other primitive data from associated sensors (20a, 20b, see block 3006 in FIG. 7),
reading information from the data and/or parameter buffers (as exemplified by block 3008) which may involve altitude data/parameters as derived from the barometric signal P produced by the sensor 12.

In one or more embodiments, the related processing may take into count timing information 3010 as possibly provided by the real time clock (block 18 in FIG. 1).

In one or more embodiments the supervisor of the expert system 3000 may be configured to "learn" a building layout (possibly in-the-field) by collecting data and extracting features in certain, possibly pre-determined configurations without the user being necessary required to insert contextual data.

Results from feature extraction as exemplified in step 3400 may involve information concerning one or more of the following entities:
the way altitude change has occurred (e.g., by lift or via staircases)
slope of the staircases used,
number of steps, climbed/descended,
climbing/descent orientation,
burned calories,
time of climbing/descending staircases,
absolute floor number,
absolute altitude (height): for instance, when an Indoor condition is detected, a reference system may pass the info of zero level on to the device 10, e. g. by Wi-Fi, Bluetooth or other communication protocols; such a zero value may be used for detecting the absolute altitude.

Such information may be exploited by any of the subunits VT, INS, PDR, W, D, F, W, S as exemplified in FIG. 1, the sensing device 10 being adapted to be configured for being compatible and capable of interfacing with such external systems.

Without prejudice to the underlying principles, the details and the embodiments may vary, even significantly, with

What is claimed is:

1. A sensing device comprising:
   a barometric sensor; and
   a processing unit coupled to the barometric sensor and configured to receive a barometric signal from the barometric sensor, the processing unit configured as a state machine having a plurality of states, the plurality of states comprising a sitting state, a walking state, a climbing a staircase in process state, and an altitude change state, wherein the state machine is configured to transition from a first state of the plurality of states to a second state of the plurality of states based on events, and wherein the state machine reaching the second state is indicative of a change in altitude of the sensing device between the first state and the second state.

2. The sensing device of claim 1, wherein the first state comprises the sitting state, the walking state, a start climbing a staircase state, the climbing a staircase in process state, or a climbing a staircase ended state, and the second state is the altitude change state.

3. The sensing device of claim 2, wherein transitioning from the first state to the second state comprises transitioning through zero or more intermediate states.

4. The sensing device of claim 1, further comprising a signal conditioning stage coupled between the barometric sensor and the processing unit and configured to provide a conditioned barometric signal to the processing unit.

5. The sensing device of claim 1, wherein the state machine is triggerable to the second state as a function of a variation in the barometric signal reaching an altitude gap threshold.

6. The sensing device of claim 1, wherein the processing unit comprises an input port configured to receive a displacement signal or a location signal, wherein the state machine is triggerable to the first state by the displacement signal or location signal.

7. The sensing device of claim 6, wherein the input port comprises a location signal input port configured to receive an indoor/outdoor signal that indicates whether the sensing device is located indoor or outdoor or a displacement signal input port configured to receive a pedometer signal or an accelerator signal.

8. The sensing device of claim 6, wherein the state machine is triggerable to the first state by the displacement signal and wherein the first state comprises a displacement state to which the state machine is triggerable as a function of the displacement signal.

9. The sensing device of claim 6, wherein the state machine is triggerable to the first state by the location signal and wherein the state machine comprises a stationary state to which the state machine is triggerable as a function of the location signal.

10. The sensing device of claim 1, wherein the processing unit comprises an expert system sensitive to state data and altitude data from the state machine to recognize the second state being reached.

11. The sensing device of claim 10, wherein the expert system is configured to perform an environment feature extraction as a function of the altitude data.

12. The sensing device of claim 11, wherein the environment feature extraction comprises one or more extracting features selected from the group consisting of:
   a manner of occurrence the change in altitude between the first state and the second state;
   a slope, a number of steps or climbing orientation of a staircase climbed/descended to lead to the change in altitude of the sensing device;
   a time taken by the change in altitude of the sensing device or calories burned by a wearer of the sensing device in the change;
   an absolute height reached as result of the change in altitude of the sensing device; and
   a floor in a building reached as result of the change in altitude of the sensing device.

13. The sensing device of claim 1, wherein the sitting state is associated with a wearer of the sensing device being in a sitting position, the walking state is associated with the wearer of the sensing device walking, and a climbing a staircase in process state is associated with the wearer of the sensing device climbing a staircase.

14. A mobile apparatus comprising:
   a barometric sensor;
   an environment sensor configured to sense displacement or location;
   a logic unit coupled to the barometric sensor and configured to receive a barometric signal from the barometric sensor, the logic unit further coupled to the environment sensor and configured to receive a displacement signal or a location signal from the environment sensor, the logic unit configured as a state machine having a plurality of states, the plurality of states comprising a sitting state, a walking state, a climbing a staircase in process state, and an altitude change state, wherein the state machine is configured to transition from a first state of the plurality of states to a second state of the plurality of states based on the barometric signal; wherein transitions triggered by the barometric signal are triggered by the barometric signal reaching a triggering threshold; and
   a processor coupled to the logic unit and configured to determine a change in altitude based upon the state machine reaching the second state.

15. The mobile apparatus of claim 14, wherein the mobile apparatus comprises a wearable device.

16. A method comprising:
   providing a barometric signal via a barometric sensor;
   processing the barometric signal with a state machine having a plurality of states, the plurality of states comprising a sitting state, a walking state, a climbing a staircase in process state, and an altitude change state;
   triggering transitions from a first state of the plurality of states of the state machine to a second state of the plurality of states of the state machine as a function of the barometric signal reaching a triggering threshold; and
   detecting a change in altitude between the first state and the second state in response to the state machine reaching the second state.

17. The method of claim 16, further comprising conditioning the barometric signal prior to processing the barometric signal.

18. The method of claim 16, further comprising receiving a displacement signal or a location signal, wherein the state machine is triggerable to the first state by the displacement signal or location signal.

19. The method of claim 16, further comprising receiving an indoor/outdoor signal that indicates whether the barometric sensor is located indoor or outdoor.

20. The method of claim 18, further comprising receiving a displacement signal input port configured to receive a pedometer signal or an accelerator signal.

21. The method of claim 16, further comprising recognizing that the second state has been reached based on state data and altitude data from the state machine.

22. The method of claim 21, further comprising performing an environment feature extraction as a function of the altitude data.

23. The method of claim 22, wherein the environment feature extraction comprises one or more extracting features selected from the group consisting of:
- a manner of occurrence the change in altitude between the first state and the second state;
- a slope, a number of steps or climbing orientation of a staircase climbed/descended to lead to the change in altitude of the barometric sensor;
- a time taken by the change in altitude of the barometric sensor or calories burned by a wearer of the barometric sensor in the change;
- an absolute height reached as result of the change in altitude of the barometric sensor; and
- a floor in a building reached as result of the change in altitude of the barometric sensor.

\* \* \* \* \*